United States Patent [19]

Muka et al.

[11] 4,119,381

[45] Oct. 10, 1978

[54] INCUBATOR AND RADIOMETRIC SCANNER

[75] Inventors: Edward Muka, Rochester; Clyde Pershing Glover, Pittsford, both of N.Y.

[73] Assignee: Eastman Kodak Company, Rochester, N.Y.

[21] Appl. No.: 751,873

[22] Filed: Dec. 17, 1976

[51] Int. Cl.² .................. G01N 21/22; G02B 5/14
[52] U.S. Cl. .................................. 356/244; 250/227
[58] Field of Search ........................ 356/36, 39–42, 356/244–246; 23/253 R; 250/227

[56] References Cited

U.S. PATENT DOCUMENTS

| | | | |
|---|---|---|---|
| 3,540,808 | 11/1970 | Harmon et al. | 356/36 |
| 3,966,322 | 6/1976 | Greaves et al. | 356/40 |
| 3,999,062 | 12/1976 | Demsky et al. | 250/227 |
| 4,038,030 | 7/1977 | Albright et al. | 23/253 R |

Primary Examiner—John K. Corbin
Assistant Examiner—Wm. H. Punter
Attorney, Agent, or Firm—D. M. Schmidt

[57] ABSTRACT

A scanner is provided for radiometric analysis of a substrate of the type which can require a controlled environment. The substrates are positioned on platforms rotated about an axis, and at least a portion of the radiometer is mounted for rotation independently of the platform rotation.

7 Claims, 11 Drawing Figures

U.S. Patent   Oct. 10, 1978   Sheet 1 of 5   4,119,381
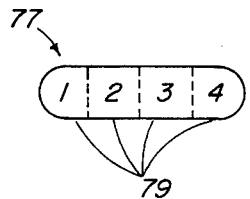
FIG. 3
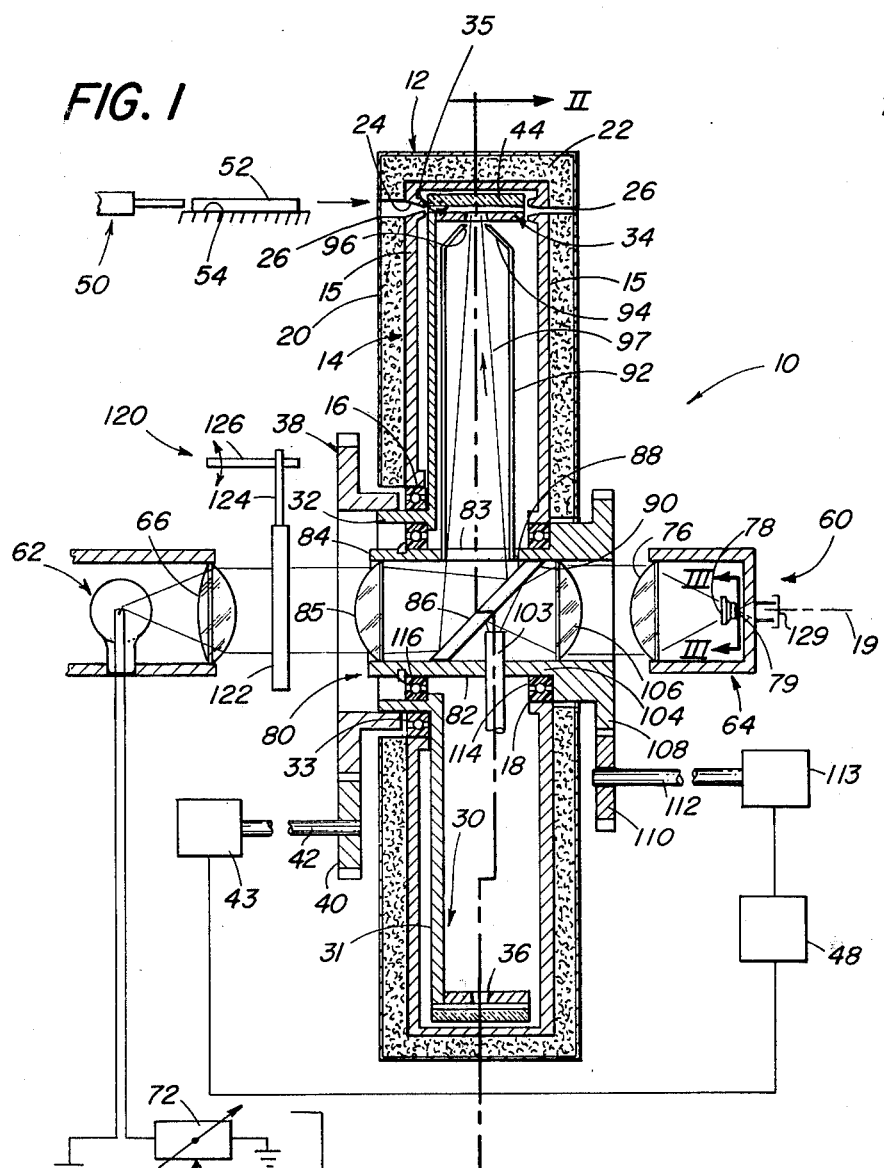
FIG. 1
FIG. 4

INCUBATOR AND RADIOMETRIC SCANNER

BACKGROUND OF THE INVENTION (1) Field of the Invention

This invention relates to a radiometric scanner and an incubator incorporating the scanner, useful for detection of the chemical state of a plurality of substrates. In a preferred embodiment the substrates are scanned optically to provide a quantitative clinical analysis of blood components.

(2) State of the Prior Art

Radiometric scanner cover a wide range of the electromagnetic spectrum. Optical scanners have been used to examine by light the contents of a substrate, such as a printed page. Although such scanners commonly move continuously across the substrate, they are not so limited and include those that obtain a reading without relative motion between the substrate and the sensor.

Some optical scanners have been designed for projecting characters from a single support station or platform using a light source and a screen, both of which are positioned on the axis of rotation of a lens system which creates sequential light beams, the lens system rotating with respect to the platform. An example is shown in U.S. Pat. No. 3,591,249. Or alternatively the substrate being read can be linearly moved through a plurality of light beams that are discontinuously formed by a lens and mirror system rotating about an axis on which the light source, receptor, and substrate support are positioned, as shown in U.S. Pat. No. 3,345,460. Such devices are not intended for use, however, in incubators.

Some conventional incubators useful for radiometrically measuring the state of a substrate, usually in liquid form, for clinical analysis generally have a plurality of stations for the substrates, often mounted for rotation about an axis, a temperature control system including a heater, and a radiometer of some type, such as a reflectometer, designed to selectively scan each of the stations. A relatively simple example of such an incubator is shown in U.S. Pat. No. 3,616,264, whereas U.S. Pat. Nos. 3,533,744; 3,756,920; 3,758,274; 3,788,816 and 3,790,346 illustrate more complex apparatus. In U.S. Pat. No. 3,533,744, flat substrates using liquid analysis are positioned tangential to a surface of revolution which they trace as they are rotated about a pair of axes formed by a conveyor system. In this art, however, no provision is made for mounting the optics of the scanner for movement, particularly for rotation, apart from the rotation of the platforms. That is, the optics are not independently mounted for rotation. As a result, the apparatus must examine in sequence each station that comes into position. However, many of the analytes of interest are desirably analyzed for a rate of reaction, with each analyte having a different rate. Problems exist in reading such rate reactions by sequentially scanning each station. A system which rotates only the substrate stations, but not the optics, necessitates a much longer search time and thus less data is available for rate analysis within a given time.

Reflectometers have also scanned the periphery of rotating stations having bacteria cultures, there being however no heaters provided as in incubators used in clinical analysis. An example is shown in U.s. Pat. No. 3,776,817. Independent motion of the optics apart from that of the stations is not provided in such devices, so that the search capability is limited.

Patents relating only to the general background of optical scanners include U.S. Pat. Nos. 3,508,065; 3,700,911 and 3,778,129.

(3) Related Applications

Commonly owned U.S. application Ser. No. 751,872 entitled "Method and Apparatus for Chemical Analysis," filed in the name of C. Glover at al on Dec. 17, 1976, now abandoned, discloses apparatus for analyzing dried substrates, including a rotating incubator.

U.S. Pat. No. 4,067,694 issued on Jan. 10, 1978 on commonly owned U.S. application Ser. No. 751,869 entitled "Loading and Unloading Mechanism for Continuously Rotating Container," filed in the name of R. Blakely et al on Dec. 17, 1976, discloses a feeding mechanism for a continuously rotating processor such as an incubator.

OBJECTS OF THE INVENTION

It is an object of the invention to provide an apparatus for scanning platforms such as can be used in an incubator, wherein the scanning mechanism is capable of searching out a particular platform without being limited to the movement given to the platforms.

It is a related object of the invention to provide such an apparatus for optically examining substrates for a rate reaction and/or end point reactions.

Other objects and advantages will become apparent by reference to the following Invention Summary and Detailed Discussion, when considered in light of the attached drawings.

SUMMARY OF THE INVENTION

The invention concerns a radiometric scanner and an incubator using such scanner, which radiometrically examines, in any order, a plurality of substrates undergoing chemical reactions in a temperature-controlled environment.

More specifically, in accordance with one aspect of the invention there is provided a radiometric scanner comprising a plurality of substrate-supporting platforms mounted for rotation around a fixed axis; means for radiometrically sensing a characteristic of the substrates at said platforms, said sensing means including a radiometer having a source of electromagnetic energy and a sensor, means for selectively directing electromagnetic energy from said source to any one of said platforms, and means for returning read-out energy from said each platform to said sensor; first means for rotating said platforms about said axis; and second means for rotating at least a portion of said sensing means with respect to said axis and said platforms, said first and second means being independently capable of activation.

By adding a means for controlling the temperature of the substrates, preferably adjacent to each platform, the apparatus becomes an incubator providing radiometric analysis under controlled temperature conditions, permitting either rate analysis or end-point analysis of chemical reactions occurring in the substrate.

In accordance with another aspect of the invention, there is provided an apparatus for the incubation of a generally flat substrate requiring controlled temperature conditions to undergo a desired chemical reaction, the apparatus comprising:

a plurality of substrate-supporting sensing stations mounted for rotation around a fixed axis, each of said stations including means for holding one of the substrates in a plane that is generally tangent to a surface of revolution traced by the center line of any one of said substrates as the one substrate is rotated about said axis;

moving means for rotating said stations about said axis; and temperature control means located adjacent to each station for maintaining each station at a desired temperature.

BRIEF DESCRIPTION OF THE DRAWINGS

FIG. 1 is a partially schematic, fragmentary sectional view of apparatus constructed in accordance with the invention;

FIGS. 2 and 3 are sectional views taken generally along lines II—II and III—III of FIG. 1;

FIG. 4 is a schematic diagram of a switching circuit useful with the apparatus of the invention;

DESCRIPTION OF THE PREFERRED EMBODIMENTS

Although the invention is hereinafter described with respect to generally planar substrates optically scanned by a light beam, the radiometer and incubator of the invention are not so limited. Any type of substrates, including liquid-containing cuvettes, and any electromagnetic energy source radiating outside of the light frequencies can be used, provided of course that suitable wave guides and/or focusing elements are used for selectively directing such outside frequencies. Thus, as used herein, "radiometric scanner" means apparatus for examining a substrate with a beam of electromagnetic energy of any suitable wavelength or band of wavelengths, such beam either continuously moving across the substrate or being temporarily fixed thereon during measurement.

Although as mentioned, any kind of substrate can be processed by this invention, a highly preferred form is a generally planar substrate of the type disclosed in Belgian Pat. No. 801,742 granted on Jan. 2, 1974, wherein a drop of blood serum is deposited onto a multilayered element, generally at the geometric center of the element, containing the necessary reagents for reacting with the analyte of choice. Certain reactions colorimetrically produce a density which is read by a reflectometer, the amount of light reflected from the element varying in accordance with the reaction and being indicative of the amount of analyte present. Other multilayered elements can produce fluorescence read by a fluorimeter wherein, from the light incident on the element, the resultant product is fluorescent emission, at a different wavelength and possibly intensified. Both sensing capabilities are present in this apparatus, as will become apparent. Thus, the apparatus is intended to radiometrically determine conditions of a substrate by detecting changes in the substrate through the broadcast of electromagnetic energy to the substrate and from the examination of the read-out energy returned from the substrate. As used herein, "read-out energy" includes electromagnetic energy having wavelengths that are different from those of the energy as initially broadcast, as well as energy of the same wavelength but at a reduced intensity.

Figure 2:
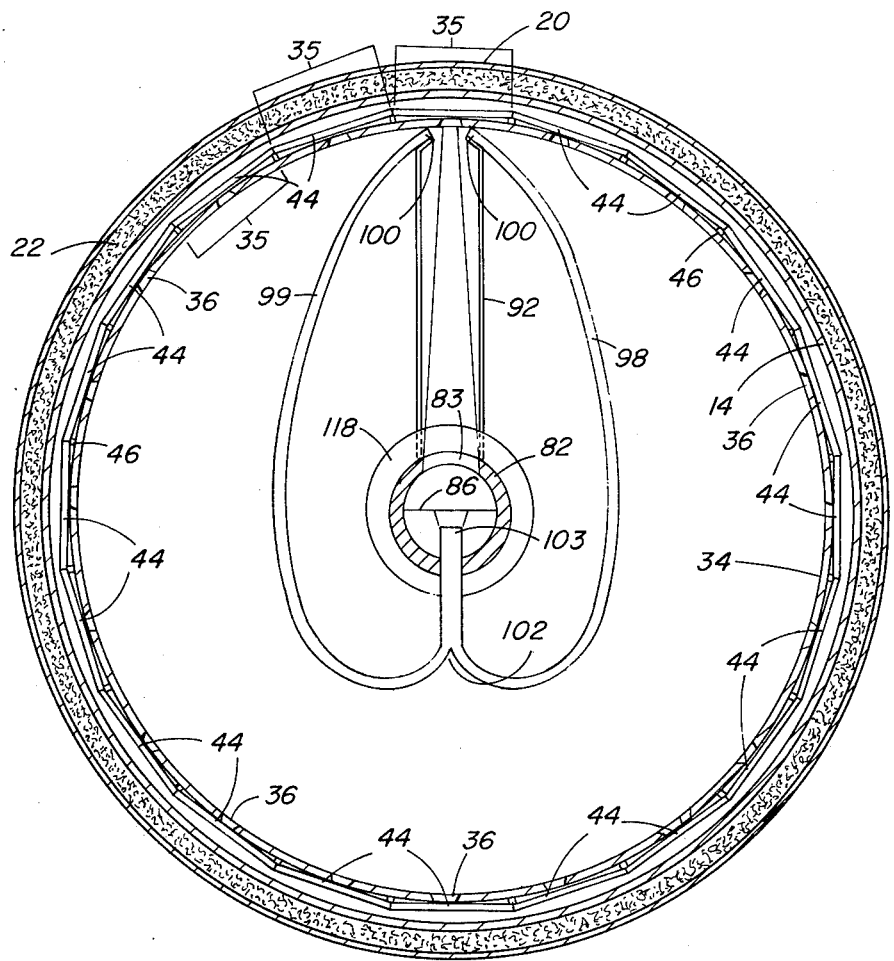

In FIGS. 1 and 2, an incubator and radiometric scanner 10 is illustrated, comprising a fixed incubator housing 12, a substrate rotor 30, means 50 for loading and unloading substrates 52 onto the rotor 30, and a radiometer 60 a portion of which is mounted in a rotor 80 separate from rotor 30.

The housing 12 comprises an inner disc 14 having spaced walls 15 each with a circular aperture 16 and 18 concentrically positioned about an axis 19 to accommodate the rotors 30 and 80. An outer wall 20 is provided to form a shield spaced from walls 15, and a layer 22 of insulation is positioned between the walls 15 and the outer wall 20. Conventional heating elements, shown schematically in FIG. 5 only, are secured to the inner face of wall 20 to guard against temperature variations that may occur in the environment of use. Preferably wall 20 and walls 15 are good thermal conductors, such as aluminum.

At one peripheral location in housing 12, load and unload slots 24 and 26 are provided in the walls 15 and 20, respectively, extending through both sides of the housing 12. The slots are generally rectangular in shape and of a size sufficient to allow the free passage of a substrate 52, as discussed hereinafter.

Mounted for rotation within the housing 12 is rotor 30, comprising a disc portion 31 and a cylindrical bearing sleeve 32 which is either integral with the disc portion, or affixed thereto. Bearing 33 separate the rotor from the housing. Disc portion 31 terminates in an annular ring 34 provided with a plurality of platforms or sensing stations 35 circumferentially positioned parallel to and substantially equidistant from axis 19 to support the substrates. Although ring 34 and thus the base for the stations 35 are cylindrical, flat planar platforms circumscribing axis 19 and preferably subtending equal angles can also be used. Even in this alternate, generally flat form, the platforms define a supporting surface which is an approximate cylinder concentric with axis 19. As a result, each substrate is positioned by stations 35 in a plane which is tangent to the surface of revolution which the center line of any one of the substrates traces as the substrates rotate about axis 19. Such an orientation is useful with a radiometer mounted for independent rotation, as described hereafter. As used herein "the center line of the substrate" refers to a line through the geometric center of the substrate which is coplanar with axis 19.

Ring 34 thus cooperates with heating members 44 to provide means for holding the substrates 52 in position for sensing.

To allow access to the substrate by light reflected by the optics as hereinafter described, ring 34 is apertured at the central portion 36 of each station, FIG. 1. The apertures are beveled in amounts sufficient to allow reflected light to be returned to the optics, as hereinafter described.

to rotate each of the stations 35 about axis 19, any suitable means can be provided. As shown in FIG. 1, an annular gear 38 is mounted or otherwise formed on the end of sleeve 32. A mated driving gear 40 mounted on drive shaft 42 engages gear 38 and provides the desired rotation of the stations to move them through a cycle from the load station represented by slots 24 and 26, and back again.

Spaced away from, but connected to ring 34 are primary heating members 44. Suitable connecting supports, such as studs 46, FIG. 2, can be used to space members 44 from ring 34. The heating members can be any conventional, flat heat-conducting pads, and when connected to rotor 30 as shown, a conventional commutator or switching mechanism is provided (not shown) to carry current to each individual pad as it rotates within housing 12. Alternatively, the heating members 44 can be affixed to the walls 15 adjacent to stations 35, so that the commutator can be eliminated.

To load and unload substrates 52 into and out of incubator 12, onto the ring 34 where they are supported for analysis, any suitable means 50 is provided. For example, a solenoid as shown can be used, or other, preferably electrically operated, linear advancing devices can be used. Appropriately treated substrates 52 are sequentially positioned onto a support 54 and moved into the incubator by means 50. When a new substrate is no loaded onto a given station 35, any previously scanned substrate already present is unloaded out the opposite side through slots 24 and 26.

As noted heretofore, scanning of the substrates is achieved by radiometer 60, which contains an energizing source 62, here an incandescent bulb of suitable radiation, and a sensor 64 for detecting the light reflected from the substrates. The source 62 emits light through a first condenser lens 66, and a servo system 68 monitors the output by conventional circuitry comprising a silicon cell 70 on which a portion of the generated beam of light is deflected by a light pipe, not shown, a suitable, conventional power supply 72, and an amplifier 74. The sensor 64 preferably comprises a cylindrical collection lens 76, filters 78, and conventional, light-detecting silicon cells 79. Both the source and the sensor are preferably located on axis 19, for reasons which will become apparent.

The source 62 and the sensor 64 are preferably fixed with respect to housing 12. However, in accordance with an important aspect of the invention, some of the optics of the radiometer are mounted on rotor 80 with means providing rotation to the optics both with respect to the fixed housing 12 and with respect to the ring 34. Such construction permits scanning of the stations in varying arbitrary sequences, such as is particularly useful in rate analysis. The tangential orientation of the substrates permits such a rotating scanner to still properly irradiate and "read" each station.

To properly scan each station with a single rotating beam, the radiometer preferably is constructed so that the beam from the source is directed, in each instance, normal to the surface of revolution formed by the rotating substrates. In the embodiment of FIG. 1, that surface is a cylinder. Accordingly, the impinging beam is also perpendicular to the axis 19; that is, is directed along radii of the incubator. To achieve this, rotor 80 comprises a cylindrical sleeve 82 having an aperture 83 at about its mid point. One end 84 of the sleeve has within it a second condenser lens 85. Mid-way along sleeve 82 and positioned within it is a reflector 86, shown in FIG. 1 as a planar mirror having two substantially parallel surfaces or sides 88 and 90. Thus sides 88 and 90 become first and second reflectors in the passage of light from source 62 to sensor 64. However, any kind of reflector can be selected, including others such as prisms and fiber-optic bundles comprising light pipes. The active reflector surfaces, namely sides 88 and 90 of mirror 86, are preferably positioned at a 45° angle to axis 19, so as to face towards and away, respectively, from aperture 83. Positioned around aperture 83 is a cylindrical light shield 92, extending radially outward from axis 19 to a beveled end 94 which is apertured at its center 96. The effect is to generate a scanning beam from reflector surface 88, shown by beam 97, that radiates outwardly from axis 19 to the stations 35.

As shown particularly in FIG. 2, also secured to rotor 80 are two light pipes 98 and 99, which have input ends 100 and are optionally joined at 102 to form a common terminus 103. Two such pipes are provided to obtain more optical power. Ends 100 are secured to the exterior of end 94 of the light shield 92, at a position which is at a 45° angle with respect to the incident light reflected perpendicularly to substrates 52, when in position, from mirror surface 88. End 103 directs the collected light, FIG. 1, back to reflector surface 90, which in turn directs the light to a collection lens 106 mounted in end 104 of sleeve 82 opposite to end 84. This lens cooperates with lens 76. An annular gear 108 is secured to or formed as part of sleeve end 104, and driving gear 110 mounted on drive shaft 112 is mated with gear 108, giving rotor 80 and it optical components a drive capability that is independent of the movement of station drive shaft 42. Rotor sleeve 82 rotates with respect to housing 12 by means of bearings 114 positioned between it and housing 12, and with respect to rotor 30 by means of bearings 116 positioned between it and rotor 30.

To provide multiple read-out capabilities for the radiometer, an optional filter wheel 120 can be provided, comprising a plurality of filters 122, only one of which is shown in FIG. 1, each mounted by an arm 124 on a rotable drive shaft 126 for movement in and out of the light beam. The filters are selected by appropriate circuitry such that, if fluorescence is to be used, the radiometer becomes a fluorimeter by inerposing an appropriate excitation filter, and by the selection of another filter, the radiometer becomes a reflectometer, as is well known.

FIG. 3 illustrates the manner in which lens 76 serves to form the returned, reflected light beam into a cylindrical beam 77 capable of being divided into four parts, each for an independent analysis. Thus, the beam can be examined in four sections, each of which is filtered by its own filter 78, 78', 78" or 78''', shown in phantom, FIG. 4, and having a specified bandpass. Each filtered section of light impinges onto a separate silicon cell 79. FIG. 4 indicates a typical manner in which the four cells can be switched for separate readings. Thus, each of the cells 79 is connected by leads 129, FIGS. 1 and 4, to a preamplifier 130 and a feedback resistor 132 to form circuits 134–137. Each of these circuits is selectively connectable via switches 144–147 to an amplifier 150 and a suitable indicating means, such as a meter 152. Alternatively, switches 144–147 can be located between cells 79 and amplifier 130.

By switching between these circuits, and therefore between filters, individually selected light frequencies can be considered. Such selectivity is useful not only because certain chemistries being studied in the substrates form indicator dyes that absorb only at certain wavelengths but also because one of the four filters can be selected to pass only light of a wavelength not absorbed by any indicator dye, thus allowing a control check of the substrate's basic reflectivity.

Figure 5:
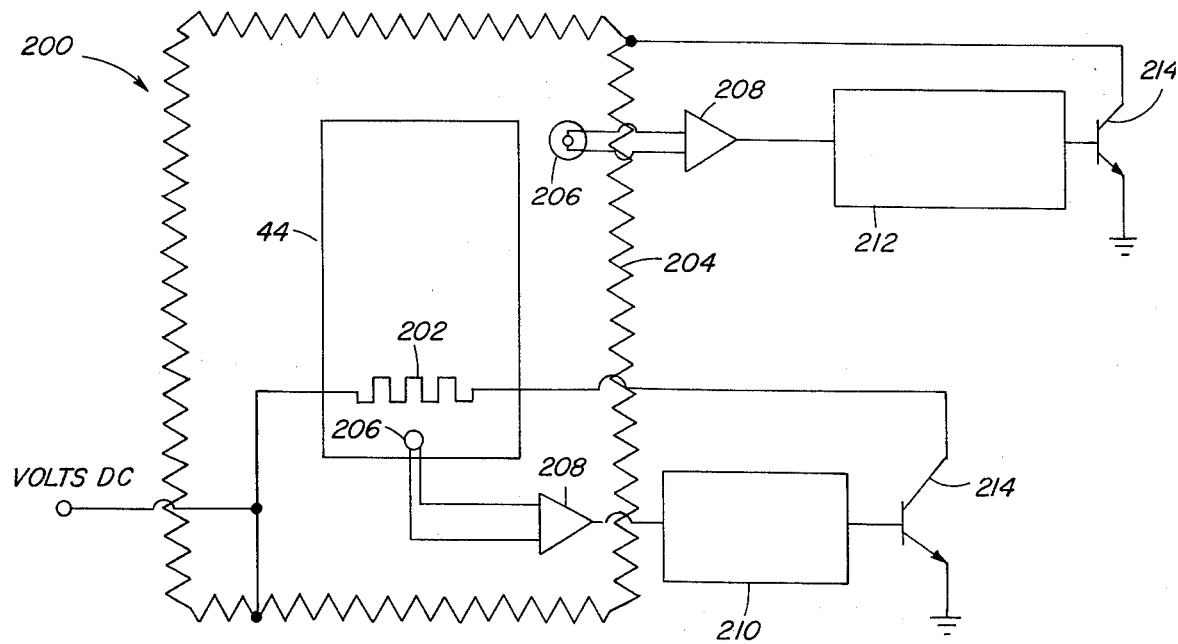
FIG. 5 is a schematic diagram of a temperature control circuit useful with the apparatus.

In FIG. 5, a typical control circuit 200 for the heating of the incubator includes primary heating element 202 physically secured to members 44, one of which is shown, and the secondary heating element 204 physically secured to wall 20. Thermistors 206 are positioned adjacent to each heating element to sense temperature changes. Electrical signals therefrom are delivered via amplifiers 208, such as bridge amplifiers, to conventional temperature control circuits 210 and 212 operating through transistors 214 to provide current to the heating elemens. Preferably, circuit 210 maintains the temperature of members 44 at about 37° C., while circuit 212 maintains shield wall at a temperature of about 30° C. Since the circuitry for such temperature controls is conventional, further details are believed to be unnecessary.

It is necessary, of course, that the apparatus sense which station 35 is being scanned. A preferred method of sensing incorporates at least one reference mark, not shown, representing a "home" station, which triggers a response by interrupting a light beam, for example, to a suitable photocell. Such reference techniques are conventional so that further description is unnecessary.

Any type of drive source can be provided for gears 40 and 110, including both continuous drives and intermittent drives. The drive mechanisms, preferably motors of any suitable type, are shown schematically as 43 and 113, respectively, wherein they are combined with conventional programmable controls. Such mechanisms 43 and 113 provide any desired speed or alternate directions of rotation on command with complete search capability, or they can be incrementally operated within a fixed predetermined program. Full computer control can be provided by any computer 48, so that the stations 35 of the incubator can be examined in any arbitrary rather than sequential pattern, due to the fact that the drive controls for the two gears are independent of each other. Thus, where 20 stations numbered 1 through 20 are available, the rates or end-points of the substrate reactions can require that beam 97 be moved, as can be dictated by computer 48, to the stations in this order: 1, 10, 15, 10, 12, 18, 1, 15, 7, 8, 9, 10, 11, 14, 16, 18, etc. In such cases the direction of rotation of the optics may be reversed. Most preferred, however, is an ordered sequence for economy of operation. Circuitry can be provided to discard readings made while both the stations and the beam are rotated, if desired, or such readings can be retained.

Inasmuch as such drive means, their timing diagrams, the logic circuits, and the computer, if used, providing necessary control are conventional and well-known, further description is unnecessary. However, the following description is provided, by way of illustration only, of various preferred modes of operation which can be utilized.

Four preferred modes of operation, all of a predetermined, fixed rate operated by mechanisms 43 and 113 using conventional programming, illustrate the flexibility of the invention. These are summarized in Table I which follows. Generally, a five minute cycle is assumed for the platforms on the basis of the fact that, within that time, most end-point reactions occurring within the substrates 52 will have been completed and the substrate can be removed from the incubator by load-unload means 50. In the intermittent movements, acceleration is neglected because such acceleration will occur only over a small portion of the times in question.

Table I

| | Mode | Platform | Optics |
|---|---|---|---|
| #1 | Stations Rotate Intermittently Optics Rotate Continuously | Increments 20 indexes in 5 minutes, 1 index lasting about 0.9 seconds, every 15 seconds. | Continuous rotation, 1 rev in 5 seconds, providing a reading $\approx 8$ msec/substrate. |
| #2 | Stations Rotate Continuously Optics Rotate Intermittently | Continuous rotation, 1 revolution in 5 minutes, requiring loading while moving. | Increments 20 indexes in 14.3 sec., 1 index lasting .25 sec. every .75 sec., providing a reading of .5 sec/substrate. |
| #3 | Stations Rotate Intermittently Optics Rotate Intermittently | Increments 20 indexes in 5 minutes, 1 index lasting 1 second, every 15 seconds. | Increments 20 indexes in 14 seconds, 1 index lasting .20 sec. every .70 sec., providing a reading $\approx .5$ sec/substrate. After every 20 reads, pauses for 0.8 sec. after next index. |
| #4 | Stations Rotate Continuously Optics Rotate Continuously | Continuous rotation, 1 revolution in 5 minutes, requiring loading while moving | Continuous rotation, 1 rev in 5 seconds, reading somewhat longer than $\approx 8$ msec/substrate. |

In the first mode, mechanism 43 can be operated to rotate gear 40 intermittently, giving intermittent rotation to the incubator ring 34, while gear 110 rotates continuously, providing continuous rotation to portions of radiometer 60. This mode provides the most rapid sequential review of all the stations. In such a case, it is preferred that the scanning beam 97 travel about axis 19 in the same direction as do the stations. A typical example of speeds of rotation would be, in the case of an incubator 10 having 20 stations and a radius of about 10 cm, a 5 minute rotation during which the stations increment 18° at a time, once every 15 seconds, taking about 0.9 seconds to increment. In the meantime, the scanning beam 97, about 3 mm in diameter, can be continuously rotated 1 revolution per 5 seconds.

The relative motion between the beam and the substrate requires data to be collected during the scan, and a 1 millimeter displacement of the beam during the scanning produces acceptable results, when the displacement is centered on the substrate. Such a displacement allows 8 milliseconds for the reading. During the 14.1 seconds the incubator stations are at rest, the beam 97 will sweep each station twice, and 17 of them three times. Three of the remaining four will be viewed while the stations move to their next position. Since the stations, when they move, move with the beam, the reading time for these three will be somewhat longer, approximately 10 milliseconds. The twentieth station will then constitute the first station to be read during the next stationary period.

In mode No. 2, the situation is reversed, that is, the stations are rotated continuously and the beam 97 rotated intermittently. A convenient program is one in which the stations complete 1 revolution in 5 minutes, as in the previously described embodiment, while the scanning beam incrementally rotates in the same direction about axis 19. In this mode of operation, the stations continually move 9/15 of 1° while beam 97 is at rest, and 9/30 of 1° while the beam is advancing. It is further desired that the beam be confined to a zone about 1 mm wide approximately centered on the stations assumed to be 18° apart. Therefore, to meet these conditions, the beam must be incrementally advanced 18.9° to catch up (9/30°) and to lead (9/15°) the stations (18° apart). The lead of 0.6° places the reading beam about 1.04 mm ahead of its last position on the last station. This last position was 0.3° or 0.52 mm lagging the center of the station. Thus, after moving, the scanning beam is 0.52 mm ahead of the center of the next station to be read. Station or ring rotation thus results in a scanning of the 0.6° or 1.04 mm in 0.5 seconds, permitting the desired reading to be made. The beam thus rotates about axis 19 in 14.3 seconds.

In mode No. 3, both the stations 35 and the beam 97 rotate intermittently. A convenient program is one in which the stations move approximately as described in the first mode, while the beam rotates as in the second mode, but covering only 18° per increment as it is not necessary to adjust for station movement. While the stations are at rest for 14 seconds, the beam will sweep all 20 stations allowing 0.2 seconds for the index and 0.5 seconds for the read. The stations will then index one increment in one second. The optics will also index one increment in 0.2 seconds and pause for 0.8 seconds without reading. The cycle is now in phase to repeat.

The fourth of the four modes is continuous rotation by both the stations and the scanning beam, again preferably in the same direction. Since the stations still preferably revolve 1 revolution per 5 minutes, each station will move through an arc of 18° in 15 seconds. The beam, however, moves through the same 18° in 0.25 seconds so that the viewing time of the preferred 1 mm spot will be slightly higher than the "rest" viewing rate in the first mode, or slightly longer than 8 milliseconds.

In those instances in which the stations are rotated intermittently, substrate loading and unloading preferably occur during the rest portion of the cycle. In those instances in which the stations are rotated continuously, loading means 50 must be made to accommodate the angular rotation so as not to interfere with such rotation. Any suitable means for providing such rotation to the loading means can be used, such as a track (not shown) following the same arc as is traced by the station to be loaded during the loading step. The solenoid retraces such a track after injecting a substrate. In such a case, slots 24 and 26 must be of greater length to accommodate such rotation of means 50.

FIGS. 6 through 11 concern an alternate loading and unloading mechanism for use with continuously rotating stations on rotor 30. Parts similar to those previously described bear the same reference numerals to which the distinguishing suffix "a" has been added.

In accordance with the invention disclosed and claimed in the commonly owned application of R. Blakely et al, Ser. No. 751,869, filed concurrently herewith, and entitled "Loading and Unloading Mechanism for Continuously Rotating Container," now U.S. Pat. No. 4,067,694, incubator 10a, FIG. 6, comprises fixed housing 12a formed by outer wall 20a and disc 14a, and rotating rotor 30a comprising stations 35a, which include notched portions 298 in a ring 34a, and heating member 44a, FIGS. 8 and 9, substantially as in the previously described embodiment. Although heating element 202a, FIG. 6, is mounted on disc 14a as fixed, high-resistance wires embedded in silicone rubber and spaced slightly away from member 44a, such a variation is not necessitated by the continuous rotation of the stations.

Figure 8:
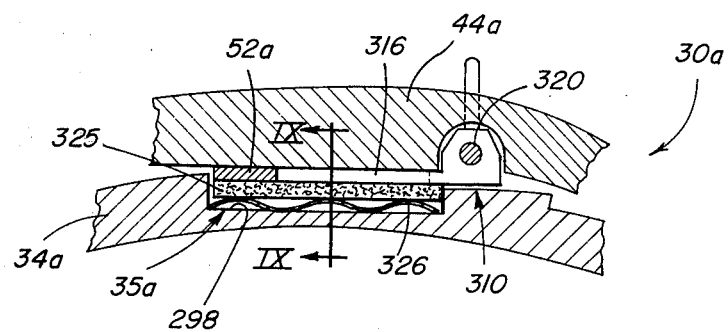
FIG. 8 is an enlarged, fragmentary sectional view similar to FIG. 2, but without the housing, illustrating the alternate embodiment.
Figure 9:
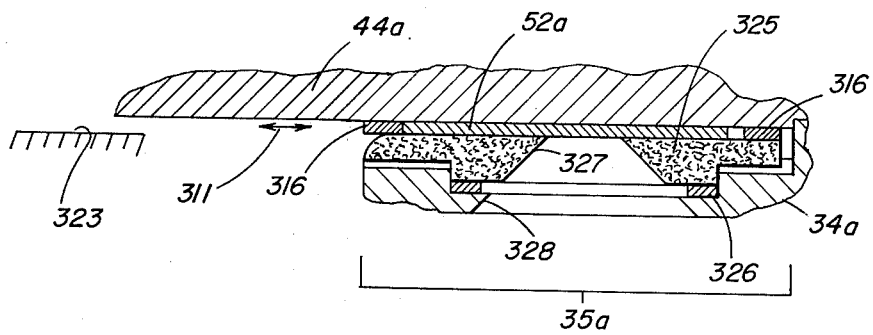
FIG. 9 is a fragmentary sectional view taken generally along the line IX—IX of FIG. 8.

Unlike the previously described embodiment, rotor 30a has the heating member 44a extending along the axis of rotation 19a, FIG. 9, a distance greater than the ring 34a extends. The heating member further includes, as disclosed in said application Ser. No. 751,869, now U.S. Pat. No. 4,067,694 above each station 35a a retractable yoke or substrate-holding frame 310, FIGS. 7-9, slidably mounted parallel to axis 19a as shown by arrow 311 on a support rod 320, moving in and out of the confines of station 35a by the action of camming members 330 and 350. Rod 320 is held in member 44a by a retaining plate 322 at each of the opposed ends 324 of rod 320, FIG. 7. Frame 310 comprises an elongated body 312 having a bore 314 longitudinally therethrough to accommodate rod 320, two spaced-apart fingers 316 extending from one side of the body in a common plane. A camming ear 318 projects generally perpendicularly from body 312 and with respect to the plane of fingers 316. Bore 314 can be a continuous aperture, or a passageway through two shoulders 319, as shown. The function of frame 310 is to capture a substrate from a stationary loading station 323, FIG. 9, and to move it onto a station 35a, as more fully described hereinafter.

Stations 35a are provided with a pressure pad 325 and a wavy spring ring 326 for holding substrates 52a in proper position against member 44a, FIGS. 8 and 9. Both the pads 325 and ring 34a at the stations are given conical apertures 327 and 328, respectively, to allow passage of the incident and reflected light beams in the manner described previously.

Figure 6:
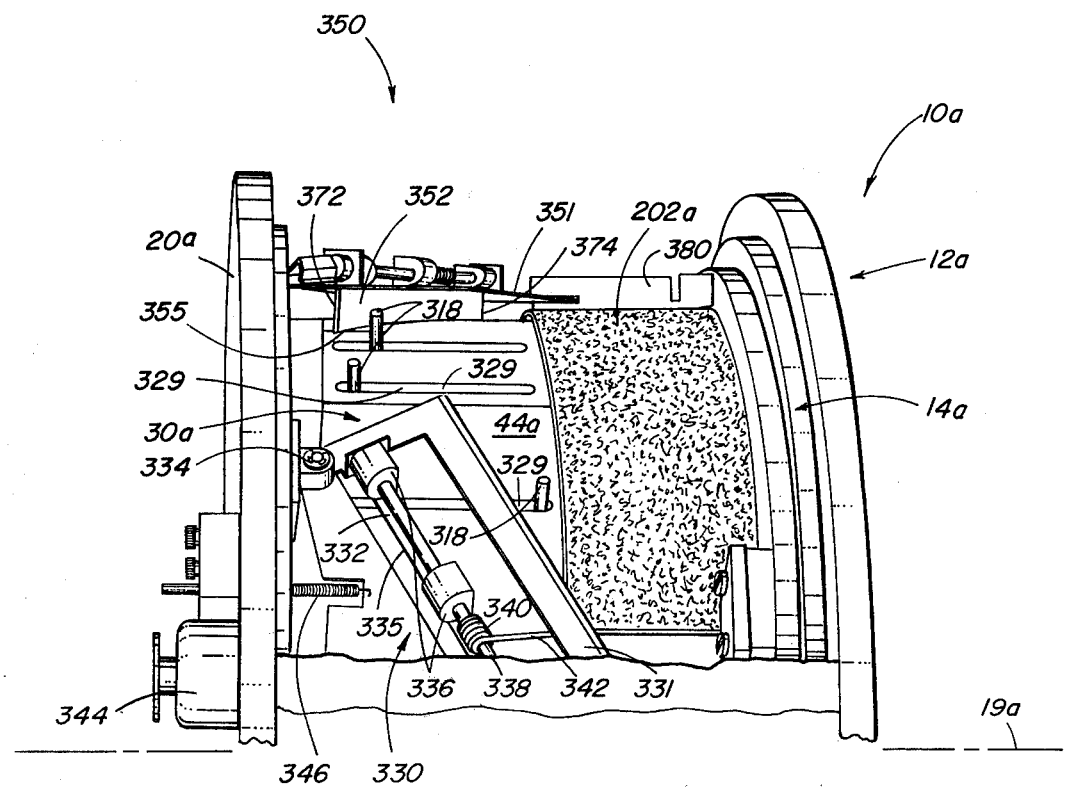
FIG. 6 is a fragmentary, partially-broken away, perspective view of another embodiment of the invention.
Figure 7:
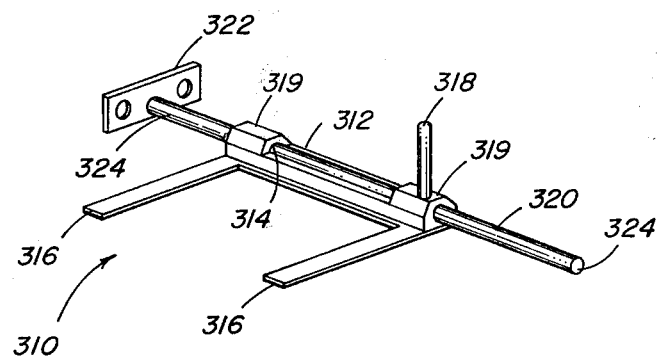
FIG. 7 is an isometric view of a substrate-holding frame utilized with the embodiment of FIG. 6.
Figure 10:
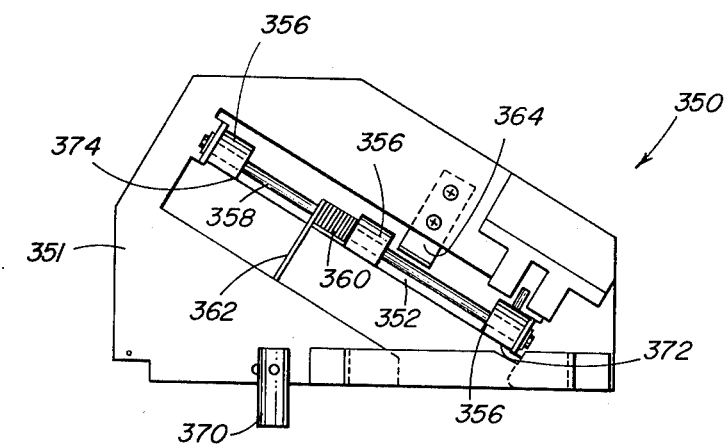
FIG. 10 is a plan view of a canning member shown in FIG. 6.

To move the frame 310 and thus the substrate 52a in and out of the confines of station 35a, FIG. 9, member 44a is slotted at 329, FIG. 6, to accommodate the axial movement of ears 318, and movable camming member 330 and fixed camming member 350 are provided, FIGS. 6 and 10, each of which includes cam blades 332 and 352, respectively, which guide ears 318 of frames 310. As shown in FIG. 6, member 330 includes a cam frame 331 pivotally attached to housing 12a by a hinge 334, blade 332 being mounted so as to depend downwardly therefrom towards rotating member 44a. Blade 332 has an edge 335 curved to conform to the curvature of rotor 30a. To permit cam blade 332 to pivot out of the way of an ear 318 that might become unable to slide, as when jammed, the blade 332 is actually pivotally mounted by lugs 336 onto a hinge pin 338 secured to frame 331. A torsion spring 340 wrapped around pin 338 with one end 342 positioned under frame 331 and the other end, not shown, affixed to the blade 332 permits the blade to rotate out of the way of a jammed ear, while applying torque that tends to maintain the blade in position against a stop, not shown, where it can engage and cam those ears 318 which are slidable.

To move cam blade 332 into and out of the path where ears 318 of frames 310 normally ride, representing the path of substrates held within stations 35a, a solenoid 344 is provided, FIG. 6. The solenoid acts via a suitable linkage, shown a linkage 345 in FIG. 11, against a return spring 346, secured to housing 12a, that holds the cam blade out of such path. Thus, FIG. 11, blade 332 is normally skewed with respect to slots 329 so as to be out of the way, as shown in phantom, of ears 318, but, when pushed by solenoid 344, is moved into the solid-line position in the path of the desired ear 318 to pull it and its frame 310 towards loading station 323. Only that amount of movement sufficient to engage the ear with pick-up end 348 of blade 332 is given to linkage 345 by the solenoid. Trailing end 349 aligns the frame 310 with the loading station 323.

Cam member 350, FIG. 10, is constructed similarly to that of member 330. That is, a cam frame 351 has a hinge pin 358 from which blade 352 movably depends. The blade is affixed to lugs 356 which pivot on pin 358. Torsion spring 360 wrapped around pin 358 has its free end 362 disposed under frame 351, to normally bias blade 352 against stop 364. As with cam member 330, if a frame 310 is unable to slide back into its station 35a, it is necessary that its rear 318 be allowed to continue on a curvilinear path, without movement parallel to axis 19a. The hinging of blade 352 against spring 360 allows the blade to temporarily rotate out of the way of ear 318. Cam blade 352 also has a curved edge 355, FIG. 6, to accommodate the rotating member 44a.

Although cam frame 350 can also be hingedly secured to housing 12a, it is not necessary. Instead, it is preferably secured by a mounting strap 370, FIGS. 10 and 11, to the housing so that blade 352 is permanently skewed with respect to the normal direction of travel of ears 318. A blade pick-up end 372 is disposed to catch any frame 310 by ear 318 that is at station 323, and carry it all the way back into station 35a, where ear 318 clears the trailing end 374 of blade 352. A guide plate 380, FIG. 6, can also be used to support the side of frame 351 opposite to that secured by strap 370.

Figure 11:
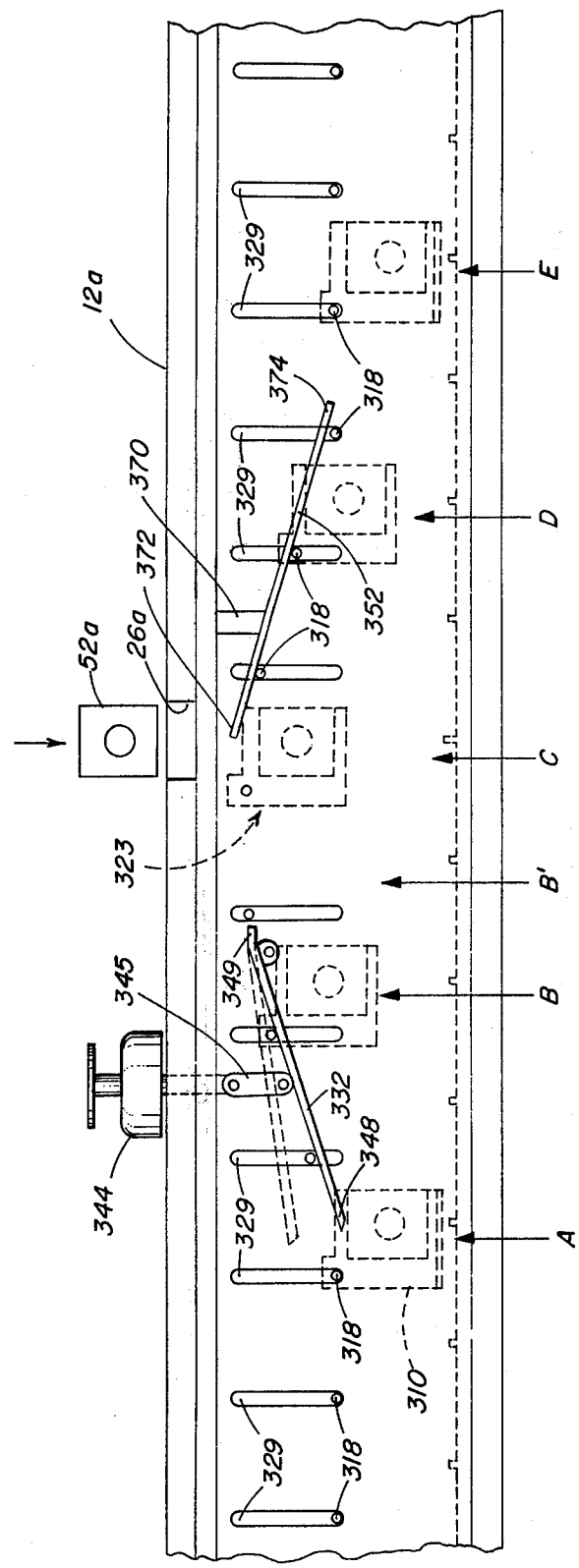
FIG. 11 is a schematic illustration of the operation of the embodiment of FIG. 6.

FIG. 11 further illustrates the sequence of operations identified above. For clarity, the circumference of the incubator has been displayed as though flat, instead of curved as in actual practice. Frames 310, shown in phantom, normally ride within their stations, as shown by position A, where they can be viewed at any time by the scanning beam heretofore described. In this position, ears 318 are at the innermost end of slots 329. If a certain station, and its frame 310, is to be provided with a new substrate 52a, cam member 330 and therefore blade 332 is pushed into the path of the desired ear 318 by solenoid 344. The ear and frame are cammed out of the station 35a towards loading station 323, as shown at position B. A cavity disposed under member 44a adjacent to the stations 35a, before station 323 is reached, position B', allows expended substrates previously incubated and examined to drop out of the frame 310. In the meantime, a new substrate 52a shown in solid lines has been fed to station 323 through slot 26a in housing 12a, and rests on station 323. Frame 310 catches the substrate between its fingers, position C, and immediately encounters cam blade 352 at its end 372 which forces ear 318 and frame 310, position D, to move back towards its station 35a that has been keeping pace with the frame 310. After ear 318 clears trailing end 374, the frame and therefore the substrate are fully seated within the station between the pressure pad and the heating member, position E.

Unless successive frames 310 are all to be given new substrates, cam blade 332 is pushed into the solid-line position only long enough to pick up the desired frame 310, after which solenoid 344 is released and spring 346, FIG. 6, returns the cam blade 332 to the dotted line position.

The pick-up and trailing ends of the cam blades can be any shape, including curved shapes for smoother transition of the movement of ears 318.

Yet another alternate embodiment, not shown, is one in which the stations of the substrate lie on the surface of a truncated cone. In such an arrangement, the planes of the substrates are, as before, tangent to that surface. However, the impinging beam of the radiometer, while normal to the substrates, is of course no longer perpendicular to the axis of rotation of the incubator.

The invention has been described in detail with particular reference to certain preferred embodiments thereof, but it will be understood that variations and modifications can be effected within the spirit and scope of the invention.

What is claimed is:

1. Apparatus for radiometric analysis of a substrate requiring controlled temperature conditions to reach a desired measurable state, the apparatus comprising
   a plurality of substrate-supporting platforms mounted for rotation around an axis;
   temperature control means for maintaining each platform at a desired temperature; and
   means positioned on said axis for radiometrically sensing a characteristic of the substrates at said platform, said sensing means including a radiometer having a source of electromagnetic energy and a sensor aligned with said axis, a first reflector positioned to selectively deflect electromagnetic energy from said source to any one of said platforms, a second reflector positioned to reflect readout energy from said any one platform to said sensor, said reflectors being integrally attached and comprising a two-sided mirror positioned at an angle of approximately 45° with respect to said axis, and a pair of light pipes, one end of each pipe being positionable adjacent to the space occupied by each of the platforms to receive reflected light therefrom and the other end of each pipe being positioned to direct light upon said second reflector; said platforms and at least a portion of said sensing means being mounted for rotation about the axis.

2. An apparatus as defined in claim 1 and further including means for loading and for unloading a substrate onto and from, respectively, said platform.

3. Apparatus as defined in claim 1, wherein said axis is the sole axis of rotation of said platforms, and further including at each of said platforms means for holding a substrate in a plane that is generally tangent to a surface of revolution traced by the center line of any one of he substrates as the one substrate is rotated about said axis.

4. An apparatus as defined in claim 1, and further including first means for rotating said platforms about said axis, and second means for rotating at least a portion of said sensing means with respect to both said axis and said platforms, said first and second means being independently activatable.

5. An apparatus as defined in claim 4 wherein said first and said second means each include control means for continuously rotating said platforms and said sensing means portion, respectively, about said axis.

6. An apparatus as defined in claim 4 wherein said first and said second means each include control means for intermittently rotating said platforms and said sensing means portion, respectively, about said axis.

7. An apparatus as defined in claim 4 wherein said first and second means include a first control means for intermittently rotating one of (a) said platforms and (b) said sensing means portion about said axis and a second control means for continuously rotating the other of (a) said platforms and (b) said sensing means portion about said axis.

* * * * *

UNITED STATES PATENT AND TRADEMARK OFFICE
CERTIFICATE OF CORRECTION

PATENT NO. : 4,119,381
DATED : October 10, 1978
INVENTOR(S) : Edward J. Muka and Clyde P. Glover It is certified that error appears in the above–identified patent and that said Letters Patent are hereby corrected as shown below:

```
Column 12, line 36 (claim 1), "platform" should read
--platforms--; line 53 (claim 1), "the axis" should read
--said axis--; line 56 (claim 2), "platform" should read
--platforms--; line 61 (claim 3), "of he" should read
--of the--.
```

Signed and Sealed this

First Day of May 1979

[SEAL]

Attest:

RUTH C. MASON
Attesting Officer

DONALD W. BANNER
Commissioner of Patents and Trademarks